(12) United States Patent
Hattori et al.

(10) Patent No.: US 9,163,251 B2
(45) Date of Patent: Oct. 20, 2015

(54) MATURE LEAF-SPECIFIC PROMOTER

(75) Inventors: Etsuko Hattori, Toyota (JP); Satoru Nishimura, Nagoya (JP); Kazuyo Ito, Kariya (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 222 days.

(21) Appl. No.: 13/976,836

(22) PCT Filed: Dec. 28, 2011

(86) PCT No.: PCT/JP2011/007337
§ 371 (c)(1),
(2), (4) Date: Jun. 27, 2013

(87) PCT Pub. No.: WO2012/090499
PCT Pub. Date: Jul. 5, 2012

(65) Prior Publication Data
US 2013/0291231 A1    Oct. 31, 2013

(30) Foreign Application Priority Data
Dec. 28, 2010 (JP) ................................ 2010-293783

(51) Int. Cl.
*C12N 15/82*   (2006.01)
*C07K 14/415*   (2006.01)

(52) U.S. Cl.
CPC .......... *C12N 15/8225* (2013.01); *C07K 14/415* (2013.01)

(58) Field of Classification Search
None
See application file for complete search history.

(56) References Cited

U.S. PATENT DOCUMENTS

2006/0141495 A1* 6/2006 Wu ................................. 435/6

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Potenza et al., in Vitro Cell Dev Biol Plant 40:1-22 (2004).*
Alignment of SEQ ID No. 1 v SEQ ID No. 22015.*
ER725945GenBank2010.*
"Analysis of the genome sequence of the flowering plant *Arabidopsis thaliana*", Nature, Dec. 2000, pp. 796-815, vol. 408.
Alan H. Christensen et al., "Maize polybiquitin genes: structure, thermal perturbation of expression and transcript splicing, and promoter activity following transfer to protoplasts by electroporation", Plant Molecular Biology, 1992, pp. 675-689, vol. 18.
Gil A. Enriquez-Obregon et al., "Herbicide-resistance sugarcane (*Saccharum officinarum* :.) plants by Agrobacterium-mediated transformation", Planta, 1998, pp. 20-27, vol. 206.
Stephen A. Goff et al., A Draft Sequence of the Rice Genome (*Oryza sativa* L. ssp. *japonica*), Science, Apr. 2002, pp. 92-100, vol. 296.

* cited by examiner

*Primary Examiner* — Medina A Ibrahim
*Assistant Examiner* — Russell Boggs
(74) *Attorney, Agent, or Firm* — Sughrue Mion, PLLC

(57) ABSTRACT

The present invention provides gene expression regulatory DNA having activity of promoting gene expression in a mature-leaf-specific manner. The following is provided: gene expression regulatory DNA having activity of promoting gene expression in a mature-leaf-specific manner, which comprises any one of the following (a) to (d): (a) DNA consisting of the nucleotide sequence shown in SEQ ID NO: 1 or SEQ ID NO: 4; (b) DNA consisting of a nucleotide sequence that has a deletion, a substitution, an addition, or an insertion of one or a plurality of nucleotides in the nucleotide sequence shown in SEQ ID NO: 1 or SEQ ID NO: 4 and having activity of promoting gene expression in a mature-leaf-specific manner; (c) DNA consisting of a nucleotide sequence having 90% or more sequence identity to the nucleotide sequence shown in SEQ ID NO: 1 or SEQ ID NO: 4 and having activity of promoting gene expression in a mature-leaf-specific manner; and (d) DNA hybridizing under stringent conditions to DNA consisting of a sequence complementary to a part or the entirety of the nucleotide sequence shown in SEQ ID NO: 1 or SEQ ID NO: 4 and having activity of promoting gene expression in a mature-leaf-specific manner.

4 Claims, 6 Drawing Sheets

Fig. 1

```
   1 ACGCACCCAG CCACTCACTC AGAACGAAAG CCCCAGCAAG CTCAGCTCAG CTGCTCACAC
  61 CTCACACCCA CAGGCCACAC TCACAGCGGA TCAGAGTAGT GAGCACTGAG CAGGGCAGCA
 121 GAGCGCGCGG TCAGTTCAGG TCGATCGTCA GCCATGAGCA AGGATGACAA GCACCACCGC
 181 CACGAGCACC ACCTGCGTCG CTGCTGCGGG TGCATGGCGT CGTGCCTGCT GGCGCTGGTC
 241 CTCATCGTCG CCTTCATCGC GCTGGTCATC TACCTCGCCC TCCGCCCCTC GAAGCCGTCC
 301 TTCTACCTGC AGGACCTGCA GCTGCGGCGG CCCATCTCGC TGGCCGACCC GTCGCTGACG
 361 GCGTCGGCGC AGGTGACGCT GGCGTCCCGC AACCCAACG AGCACGTGGG CATCTTCTAC
 421 AAGCGCCTGG ACGTGTTCGT GACCTACCAG AACGAGGCGG TCACGGTGCC CGTGTCGCTG
 481 CCGGCGCAGT ACCAGGGCCA CCGCGACGTC ACCCCGTGT CCCCGTGCT GTCGGCCGAG
 541 TCCGTGCCCG TGGCCCGGCTA CGTCGCCGAC GACCTCAAGC GTGACGTCGC GGCCGGCTTC
 601 GTCGCTCTGC AGGTCAAGGT GGACGGCCGC GTCAAGTGGA AGGTCGGCAG CTGGGTCTCC
 661 GGGAGCTACC ACCTCTTCGT CAGCTGCCCC GCCGTGCTCT CCGCGGGGTA CCCCGGCGTC
 721 GTGGGCGGCG GCGGCAACAA CACCGTGTCG TCGCTCAAGT TCGCGCAGCC CACGAGCCAA
 781 AGCGTCGAGG TGTGATGTGA TCCACCGTAG ACGCACTCAA GAACAGTTGC CAAGTACTGC
 841 TACTCAAATT TCTTTGGGTA CACCGTTAAT TACGCTGTTA ATTTTGTTCA TGTCTCATTC
 901 TCAATTCTCA TTCTCTTGTG GGGAATAAGT TTCTGTCGCA GGCCATATAG CTGTTCAAAA
 961 ACTTGAAGTC AATTGTACCA ACATGTGTTT ATTCAAAGAA GAAAAGAGGG CCACTGCAAA
1021 AACATACATA GATGCGCTAA CCCCGAGCAT GCTCAAAACT AGAAGAACTC CCACCGACGC
1081 CTATAGTGGC GACTGAAATAC TGCCACAAAC TCGGGGGGG CGCCTAAAAG ATTCACATCT
1141 AATTTCGCTG TGTGGAAAGA ATTAATCCTC TCGGAGGGGC CCAAAAATAA GGCACCGGGC
1201 CCCAGTTTAA AAGAGGATGA GGGGAGAAAC ACCGGCGTTC ACAAAATATA ATGCCCTTGA
1261 CAGTAAACCC TCCCTTCTAC CATGGGGTGT ATAAACAATA AAAGGCCACA CCTATAAGGC
1321 C
```

Fig. 3

HindIII

AAGCTT GATC TGTGGTATTT TGGACTTCTA TTACAAGTTT ACAGACACAG GGCTCATCTG
CAGTCGGTGG GGGAGATAAG GAGCGAATGG AGGGGCACAA ATGTGACGCC ACGCCGGGGA
AGGTTCTCTG ATCGGAGTGT ATTACGGACG GGCCGTCTGC TCCGTCGGCG TTTTGGGCTT
TTGGGGTAGG GCGGATGGAC TCGACGTCGG AACTACCAAC ATGATGATTG ATGAACGCGC
GCCCGACGCA TTGGCGCGTG CGTCCGTGCC TCCGTGCTTG CTACGCCCCA CCAACCTTCT
CCACTACGCC CGGACAAATG CCGTGGCAAG GAGGCACAAC ACCCACGCTA ACTAACGCTC
ATATAATCAA CTTTGTACTA TTTGTATAGT TATTAAACTG GCAGCATTCC AAGAAATGAC
CGCACGTTAA TCCTTCTGA CTGCCTATTG CCAACCGTTC CTTTCTAGA CCCCATCCAT
CCAGTTCCAA ACAAGATGTA TTAGAAATGC TTACATGTGT AAATATATGT ACATAAATAC
TGCTTGCCTC GTTTTCATT CATTATTTAA AACTATGACT GAGTTTGATA TGTAGTAGTT
TTGCATTGAT TGGCACACAA TATGTATAAT GAGAGTGTGT CAAACTTTCC TCCTCATTTT
CACTCATCCA AATTCGATGC ACGAATCCCT ACGGCCACAA CCGACTATTA AGAATAGTCC
AATTTGGCAC TACTCTAAAT AGTTGCTGGA GTTTGATGTT GTCTCTCCAA CTCCAACACG
GATATCTTGT GCGCTCCAGC TGCAAAACCA TTTATCACTA CACATTAGCA TCCTCCTCAT
CCTTTTCTTC CAACCATCGC CTCTCATGGT TTGCGATAAG GATGGGGTGG AGCGATCCAT
GTATCTCCTC TAGTTCAACT TAATGAAATA TATGTGCGAA AACAAGGCAA GGAATTGTCT
AATTAGCTCT TTCAGTTGAA ACCAGAGGCG AACCACATAT ACTCATCGGA ACATCATCCC
CATCCTTAGT TTGGGAGACA TTGATCTCAT GATCTGTCAA GGCGTTAGAG CTAGCGTTGC
CTTGTTGAAC ATTGGCTTTG ATGTTGCAAA GACTACATCG CTTCATTAAG GGGTCGAAGA
CGTGGAAATT GTGCAGGACG AAGCAAAAGC CACACACTGC GTTGTTTGAA TACTTCACCG
TAATTCTTGG TTCAAGCTTT GAGCATACAA CCAGAATCAA TCTTGTCTTG AAGCCTTAGT
CTTGCAATCC ACCAACCTCA GCGACCTTGA CGCTTGCTTC TCGGAGGCAA AAGTTTTGTC
AGTGATCAAT GACATTTCAT CAGACAAGGC GACATTACCG GACGGGTTCA CTGGGCTCTT
CTACCAACGC CGCATCAAAC AAGCCCCAGA GATGTAAAAC AAACAGTTTA TATACATAAT
TAAAACTAGT AAATTCAAGC GTGGCCGAGT GAATCTCAAG CTGACGTGTG TAGTTCCCGC
CGTCGCACTC AAGAAAGGTC AAAGGTGGAC ACGAATCTCA AAGCAATGCA TATGCATATG
CACATGCACA AGCACAACCC GACGTCCCCG TGCCAGACCC GGTGGCCCAC CGGATGAAGT
ACGTACCGAA TTAGCAGATG GAGGAATCTT CTTCGGTTGA GACGTTGCTT TCCGCTACAC
CTTCTCTGCC AGTCTGCTGT CTGCTCTGCT GCAGGCTGTC TGCTAGCTGA GCCCTGCAG
GTGATGTGCT AGCTTTTGAG TGGCACATGC GCTGTGTTTG TGTAGTCTAG TGTAGCCGGC
GTAGCAACGC TTGGTGTGCC ACTACCGATT TTAAAAGCCA TTACGCTTTC CTACACCGCA
CGGCTCAGTC ACCCACCCAC CCACTCACTC AGAACGAAAG CCCCAGCAAG CTCAGCTCAG
CTGCTCACAC CTCACACCCA CAGGCCACAC TCACAGCGGA GCAGAGTAGT GAGCACTGAG
CAGGGCAGCA GAGCGCGCGG TCAGTTCAGG TCGATCGTCA GCC ATG CCTA GG
                                        Initiation  BlnI
                                        codon

Fig. 4-1

Processed sequence:

```
   1    AAGCTTGATCTGTGGTATTTTGGACTTCTATTACAAGTTTACAGACACAG
  51    GGCTCATCTGCAGTCGGTGGGGGAGATAAGGAGCGAATGGAGGGGCACAA
 101    ATGTGACGCCACGCCGGGGAAGGTTCTCTGATCGGAGTGTATTACGGACG
 151    GGCCGTCTGCTCCGTCGGCGTTTTGGGCTTTTGGGGTAGGGCGGATGGAC
 201    TCGACGTCGGAACTACCAACATGATGATTGATGAACGCGCGCCCGACGCA
 251    TTGGCGCGTGCGTCCGTGCCTCCGTGCTTGCTACGCCCACCAACCTTCT
 301    CCACTACGCCCGGACAAATGCCGTGGCAAGGAGGGACAACACCCACGCTA
 351    ACTAACGCTCATATAATCAACTTTGTACTATTTGTATAGTTATTAAACTG
 401    GCAGCATTCCAAGAAATGACCGCACGTTAATTCCTTCTGACTGCCTATTG
 451    CCAACCGTTCCTTTTCTAGACCCCATCCATGCCAGTTCCAAACAAGATGT
 501    ATTAGAAATGCTTACATGTGTAAATATATGTACATAAATACTGCTTGCCT
 551    CGTTTTTCATTCATTATTTAAAACTATGACTGAGTTTGATATGTAGTAGT
 601    TTTGCATTGATTGGCACACAATATGTATAATGAGAGTGTGTCAAACTTTC
 651    CTCCTCATTTTCACTCATCCAAATTCGATGCACGAATCCCTACGGCCACA
 701    ACCGACTATTAAGAATAGTCCAATTTGGCACTACTCTAAATAGTTGCTGG
 751    AGTTTGATGTTGTCTCTCCAACTCCAACACGGATATCTTGTGCGCTCCAG
 801    CTGCAAAACCATTTATCACTACACATTAGCATCCTCCTCATGCTTTTCTT
 851    CCAACCATCGCCTCTCATGGTTTGCGATAAGGATGGGGTGGAGCGATCCA
 901    TGTATCTCCTCTAGTTCAACTTAATGAAATATATGTGCGAAAACAAGGCA
 951    AGGAATTGTCTAATTAGCTCTTTCAGTTGAAACCAGAGGCGAACCACATA
1001    TACTCATCGGAACATCATCCCCATCCTTAGTTTGGGAGACATTGATCTCA
1051    TGATCTGTCAAGGCGTTAGAGCTAGCGTTGCCTTGTTGAACATTGGCTTT
1101    GATGTTGCAAAGACTACATCGCTTCATTAAGGGGTCGAAGACGTGGAAAT
1151    TGTGCAGGACGAAGCAAAAGCCACACACTGCGTTGTTTGAATACTTCACC
1201    GTAATTCTTGGTTCAAGCTTTGAGCATACAACCAGAATCAATCTTGTCTT
1251    GAAGCCTTAGTCTTGCAATCCACCAACCTCAGCGACCTTGACGCTTGCTT
1301    CTCGGAGGCAAAAGTTTTGTCAGTGATCAATGACATTTCATCAGACAAGG
1351    CGACATTACCGGACGGGTTCACTGGGCTCTTCTACCAACGCCGCATCAAA
1401    CAAGCCCCAGAGATGTAAAACAAACAGTTTATATACATAATTAAAACTAG
1451    TAAATTCAAGCGTGGCCGAGTGAATCTCAAGCTGACGTGTGTAGTTCCCG
1501    CCGTCGCACTCAAGAAAGGTCAAAGGTGGACACGAATCTCAAAGCAATGC
1551    ATATGCATATGCACATGCACAAGCACAACCCGACGTCCCCGTGCCAGACC
1601    CGGTGGCCCACCGGATGAAGTACGTACCGAATTAGCAGATGGAGGAATCT
1651    TCTTCGGTTGAGACGTTGCTTTCCGCTACACCTTCTCTGCCAGTCTGCTG
```

Fig. 4-2

| | |
|---|---|
| 1701 | TCTGCTCTGCTGCAGGCTGTCTGCTAGCTGAGCCCTGCAGCGAGGGTTAA |
| 1751 | CCAATCGTCCATTCGTGATGTGCTAGCTTTTGAGTGGCACATGCGCTGTG |
| 1801 | TTTGTGTAGTCTAGTGTAGCCGGCGTAGCAACGCTTGGTGTGCCACTACC |
| 1851 | GATTTTAAAAGCCATTACGCTTTCCTACACCGCACGGCTCAGTCACCCAC |
| 1901 | CCACCCACTCACTCAGAACGAAAGCCCCAGCAAGCTCAGCTCAGCTGCTC |
| 1951 | ACACCTCACACCCACAGGCCACACTCACAGCGGAGCAGAGTAGTGAGCAC |
| 2001 | TGAGCAGGGCAGCAGAGCGCGCGGTCAGTTCAGGTCGATCGTCAGCCATG |
| 2051 | CCTAGGN |

 : Predicted promoter region (An HindIII restriction enzyme recognition sequence (AAGCTT) and a BlnI restriction enzyme recognition sequence (CCTAGG) are present at the 5'-end and the 3'-end, respectively.)

Proscan: Version 1.7
Processed Sequence: 2057 Base Pairs

Promoter region predicted on reverse strand in 1669 to 1419
Promoter Score: 64.48 (Promoter Cutoff = 53.000000)
TATA found at 1437, Est.TSS = 1405
Significant Signals:

| Name | Strand | Location | Weight |
|---|---|---|---|
| AP-2 | + | 1607 | 1.091000 |
| Sp1 | - | 1502 | 3.191000 |
| Sp1 | + | 1497 | 3.119000 |
| ATF/CREB | - | 1488 | 1.564000 |
| E4F1 | - | 1488 | 1.201000 |
| NF-S | - | 1487 | 1.019000 |
| CREB | + | 1483 | 5.737000 |
| ATF | + | 1483 | 1.591000 |
| UCE.2 | + | 1464 | 1.216000 |
| TFIID | - | 1435 | 1.971000 |
| TFIID | - | 1433 | 2.618000 |

MATURE LEAF-SPECIFIC PROMOTER

CROSS REFERENCE TO RELATED APPLICATIONS

This application is a National Stage of International Application No. PCT/JP2011/007337 filed Dec. 28, 2011, claiming priority based on Japanese Patent Application No. 2010-293783 filed Dec. 28, 2010, the contents of all of which are incorporated herein by reference in their entirety.

TECHNICAL FIELD

The present invention relates to gene expression regulatory DNA having activity of promoting gene expression in a mature-leaf-specific manner and the use thereof.

BACKGROUND ART

Genetic information of an organism is transmitted through a series of processes referred to as "central dogma" in which the DNA information of a functional gene is transcribed into mRNA and a functional protein is synthesized via translation of mRNA information. As a result, a biofunction is expressed. Genomic DNA is an aggregate of genetic information formed via association of parent haploids. Also for plants, genomic DNA generally specifies the nature of cells containing the DNA and a plant derived from such cells.

For the purpose of inducing expression of the biofunction through transmission of functional genetic information of genomic DNA contained in cells in a correct manner, it is necessary to induce expression of an adequate gene with adequate timing at an adequate site and with an adequate intensity. Therefore, strict regulation of the expression of specific genes is required.

For the expression of a functional gene, the time, site, and intensity of expression are regulated by the gene expression regulatory DNA which presents in the 5' upstream region of the gene.

In recent years, as a result of the deciphering of genomic DNA using *Arabidopsis thaliana*, rice, and the like, it has become possible to readily obtain gene expression regulatory DNAs of individual functional genes of such plants (Non-Patent Documents 1 and 2).

Meanwhile, genomic DNA of sugarcane, which is a readily available crop, has not been deciphered yet. Therefore, it is not easy to obtain gene expression regulatory DNAs of individual functional genes of sugarcane. Hitherto, for gene introduction into sugarcane, gene expression regulatory DNA from a non-sugarcane plant has been used to regulate expression of a transgene (Non-Patent Documents 3 and 4).

However, when functional gene expression is induced in sugarcane using gene expression regulatory DNA of a non-sugarcane plant, it is observed in some cases that the time, site, intensity, and other conditions of expression cannot be strictly regulated. Therefore, acquisition of sugarcane-derived gene expression regulatory DNA, and particularly, tissue-specific gene expression regulatory DNA, has been awaited in the related fields.

CITATION LIST

Non Patent Literature

NPL 1: Nature, 2000, 408:769-815
NPL 2: Science, 2002, 296:92-100
NPL 3: Plant Mol Biol. 1992, February; 18 (4):675-89
NPL 4: Planta, 1998, 206:20-27

SUMMARY OF INVENTION

Technical Problem

Therefore, an object of the present invention is to provide gene expression regulatory DNA having activity of promoting gene expression in a mature-leaf-specific manner.

Solution to Problem

As a result of intensive studies to achieve the above object, the present inventors found gene expression regulatory DNA having activity of promoting gene expression in a mature-leaf-specific manner in the 5' upstream region of a gene expressed in mature leaves of sugarcane. This has led to the completion of the present invention.

Specifically, the present invention encompasses the following features {1} to {4}.

{1} A gene expression regulatory DNA having activity of promoting gene expression in a mature-leaf-specific manner, which comprises any one of the following (a) to (d):

(a) DNA consisting of the nucleotide sequence shown in SEQ ID NO: 1 or SEQ ID NO: 4;

(b) DNA consisting of a nucleotide sequence that has a deletion, a substitution, an addition, or an insertion of one or a plurality of nucleotides in the nucleotide sequence shown in SEQ ID NO: 1 or SEQ ID NO: 4 and having activity of promoting gene expression in a mature-leaf-specific manner;

(c) DNA consisting of a nucleotide sequence having 90% or more sequence identity to the nucleotide sequence shown in SEQ ID NO: 1 or SEQ ID NO: 4 and having activity of promoting gene expression in a mature-leaf-specific manner; and (d) DNA hybridizing under stringent conditions to DNA consisting of a sequence complementary to a part or the entirety of the nucleotide sequence shown in SEQ ID NO: 1 or SEQ ID NO: 4 and having activity of promoting gene expression in a mature-leaf-specific manner.

{2} A recombinant vector, which comprises the gene expression regulatory DNA according to {1}.

{3} A transformed plant obtained by transformation using the recombinant vector according to {2}.

{4} A transformed plant obtained from plant cells transformed by plant cell transformation using the recombinant vector according to {2}.

A part or all of the content disclosed in the description and/or drawings of Japanese Patent Application No. 2010-293783, which is a priority document of the present application, is herein incorporated by reference.

Advantageous Effects of Invention

According to the present invention, the following can be provided: gene expression regulatory DNA having activity of promoting gene expression in a mature-leaf-specific manner; a recombinant vector comprising the DNA, which can cause a functional gene to be expressed in a mature-leaf-specific manner; and a transformed plant transfected with the recombinant vector.

BRIEF DESCRIPTION OF DRAWINGS

FIG. 1 shows the nucleotide sequence (SEQ ID NO: 2) of *Saccharum officinarum*-derived ecc0001 EST (searched for using the DFCI Sugarcane Gene Index).

FIG. 3 shows the nucleotide sequence (SEQ ID NO: 3) of the gene expression regulatory region of the ecc0001gene (SEQ ID NO: 1) into which an HindIII restriction enzyme recognition sequence and a BlnI restriction enzyme recognition sequence were inserted at the 5'- and 3'-ends, respectively.

FIG. 4-1 shows a predicted promoter region in the gene expression regulatory region of the ecc0001 gene (SEQ ID NO: 5) identified using a promoter analysis tool.

FIG. 4-2 (continued from FIG. 4-1)

DESCRIPTION OF EMBODIMENTS

Figure 2:
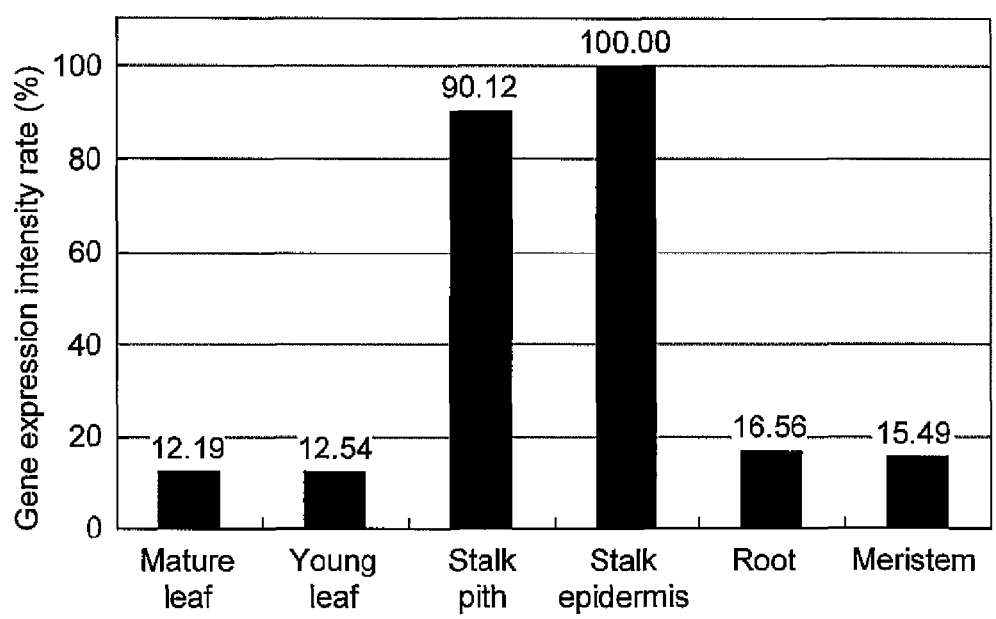
FIG. 2 shows results of ecc0001 EST expression level analysis for individual tissues of *Saccharum* spp. hybrids cv. NiF8. The strongest expression level confirmed for stalk epidermis is designated as 100.

The present invention is described in detail below.

First, the gene expression regulatory DNA having activity of promoting gene expression in a mature-leaf-specific manner of the present invention is described. The gene expression regulatory DNA of the present invention comprises any one of the following (a) to (d):

(a) DNA consisting of the nucleotide sequence shown in SEQ ID NO: 1 or SEQ ID NO: 4;

(b) DNA consisting of a nucleotide sequence that has a deletion, a substitution, an addition, or an insertion of one or a plurality of nucleotides in the nucleotide sequence shown in SEQ ID NO: 1 or SEQ ID NO: 4 and having activity of promoting gene expression in a mature-leaf-specific manner;

(c) DNA consisting of a nucleotide sequence having 90% or more sequence identity to the nucleotide sequence shown in SEQ ID NO: 1 or SEQ ID NO: 4 and having activity of promoting gene expression in a mature-leaf-specific manner; and (d) DNA hybridizing under stringent conditions to DNA consisting of a sequence complementary to a part or the entirety of the nucleotide sequence shown in SEQ ID NO: 1 or SEQ ID NO: 4 and having activity of promoting gene expression in a mature-leaf-specific manner.

The gene expression regulatory DNA of the present invention can be obtained in the following manner: candidate genes expressed in mature leaves are obtained by gene expression analysis using total RNAs from individual sugarcane tissues (of stalks, mature leaves, young leaves, and the like) or cDNAs from such RNAs; expression characteristics of the candidate genes are evaluated; genes evaluated as being expressed in a mature-leaf specific manner are specified based on the evaluation results; and the nucleotide sequence of the 5' upstream region of each candidate gene is identified based on cDNA or genomic DNA of the relevant specified gene. Here, gene expression analysis can be carried out using exhaustive gene expression analysis techniques generally known to persons skilled in the art such as a DNA chip method and a differential display method.

Specifically, the nucleotide sequence of SEQ ID NO: 1 or SEQ ID NO: 4 exists in the 5' upstream region of the gene (hereinafter referred to as "ecc0001") which is expressed in mature sugarcane leaves. Examples of "sugarcane" plants described herein include (but are not particularly limited to) plants belonging to the genus *Saccharum* such as *Saccharum officinarum, Saccharum sinense, Saccharum barberi, Saccharum robustum, Saccharum spontaneum, Saccharum edule*, and *Saccharum* spp. hybrids cv. NiF8; and plants belonging to a genus/species closely related to the genus *Saccharum/Saccharum* species, such as, *Sorghum* or *Erianthus*. Of these, *Saccharum* spp. hybrids cv. NiF8 is preferable.

A method for isolating DNA present in the 5' upstream region is not particularly limited. DNA isolation can be conducted by a method generally known to persons skilled in the art. For instance, DNA can be isolated by a conventionally known method comprising cloning an unknown region (i.e., the 5' upstream region in the above case) based on the nucleotide sequence (SEQ ID NO: 2) of the ecc0001 gene. In such a method, genomic DNA containing the 5' upstream region of the ecc0001 gene is subjected to restriction enzyme treatment such that an adopter consisting of a predetermined nucleotide sequence is ligated to the DNA. Primers are designated for the nucleotide sequence of the ecc0001 gene and the adopter, followed by PCR. Accordingly, an unknown nucleotide sequence adjacent to the 5' upstream region of the nucleotide sequence of the ecc0001 gene can be amplified. After the amplified nucleotide sequence is determined, another pair of primers is designed based on the determined nucleotide sequence. Thus, another unknown nucleotide sequence adjacent to the determined nucleotide sequence can be amplified in a similar manner. This method can be carried out using a commercially available cloning kit such as a RightWalk (registered trademark) kit (BEX Co., Ltd.). Alternatively, a method using inverse PCR can be suggested in addition to the above. In such case, a pair of primers is designed based on the nucleotide sequence information of the ecc0001 gene. PCR is performed using the pair of primers and a genomic DNA fragment obtained via treatment with a certain restriction enzyme and self-ligation. Thus, the upstream region of the ecc0001 gene can be amplified. Further, another method for isolating the upstream region of the ecc0001 gene from a genomic DNA library can be suggested. In such case, a genomic DNA library that has been prepared by a standard method is screened with the use of cDNA comprising the ecc0001 gene as a probe to obtain genomic DNA comprising the ecc0001 gene. Then, the nucleotide sequence of genomic DNA obtained by screening is determined. Accordingly, the 5' upstream region present in the upstream region of the ecc0001 gene can be specified. Further, the 5' upstream region alone can be amplified by PCR or the like.

As described above, unknown nucleotide sequences located upstream of the ecc0001 gene are sequentially amplified or screened for to determine the nucleotide sequence by a standard method. Accordingly, the nucleotide sequence shown in SEQ ID NO: 1 or SEQ ID NO: 4 can be specified. Once the nucleotide sequence shown in SEQ ID NO: 1 or SEQ ID NO: 4 is determined, it becomes possible to obtain the nucleotide sequence shown in SEQ ID NO: 1 or SEQ ID NO: 4 by PCR using genomic DNA extracted from sugarcane as a template and primers designed based on the nucleotide sequence shown in SEQ ID NO: 1 or SEQ ID NO: 4.

The nucleotide sequence shown in SEQ ID NO: 1 or SEQ ID NO: 4 functions as a gene expression regulatory region capable of inducing gene expression in a mature-leaf-specific manner. A gene expression regulatory region contains nucleotide sequences involved in gene transcription control, such as, a promoter region, an enhancer region, a TATA box, and/or a CAT box (although the contents of the region are not particularly limited thereto).

The word "specific" used herein refers to the following conditions: a gene expression inducible function is exclusively present in mature leaf tissue, which is one of individual tissues constituting a plant; and the gene expression inducible function in mature leaf tissue is remarkably or statistically significantly (e.g., about 2-fold, 3-fold, 4-fold, 5-fold, 6-fold, 7-fold, 8-fold, 9-fold, or 10-fold or more) greater than the gene expression inducible function in a non-mature-leaf tissue (e.g., a stalk, young leaf, root, or meristem tissue).

The term "mature leaf (tissue)" used herein refers to a leaf (tissue) that contains chloroplasts accumulating in cells for photosynthesis and thus is tinged with green. It also refers to a leaf (tissue) other than a young leaf (tissue) containing no chloroplasts for photosynthesis.

The gene expression inducible function can be confirmed by reporter assay or the like generally known to persons skilled in the art. Upon reporter assay, a vector is prepared in which various reporter genes (e.g., the beta-glucuronidase gene (GUS), the luciferase gene (LUC), and the green fluorescent protein gene (GFP)) are ligated to the downstream region of a nucleotide sequence to be examined in terms of the gene expression inducible function such that the reporter genes are regulated by the nucleotide sequence. Gene introduction (or transient gene introduction) into the genome of a host is carried out using the vector. Then, the expression level of each reporter gene is determined. Thus, the gene expression inducible function can be confirmed. The reporter gene is not particularly limited as long as the expression thereof is detectable. Examples of such reporter gene include reporter genes conventionally used by persons skilled in the art such as the CAT gene, the lacZ gene, the luciferase (hereafter denoted by "LUC") gene, the beta-glucuronidase (hereafter denoted by "GUS") gene, and the green fluorescent protein (hereafter denoted by "GFP") gene.

The expression level of a reporter gene can be determined by a method generally known to persons skilled in the art depending on the type of the reporter gene. For instance, if the reporter gene is the CAT gene, the expression level of the reporter gene can be determined by detecting acetylation of chloramphenicol with the gene product. The expression level of an individual reporter gene can be determined by the following technique. In a case in which the reporter gene is the lacZ gene, color development of a dye compound induced by the catalytic action of the gene expression product is detected. In a case in which the reporter gene is the LUC gene, fluorescence emission from a fluorescent compound induced by the catalytic action of the gene expression product is detected. In a case in which the reporter gene is the GFP gene, fluorescence emission from the GFP protein is detected. For instance, if the reporter gene is GUS, GUS activity is determined as promoter activity in a host cell by one of both of the following methods: (i) a method involving histochemical GUS staining (EMBO J. 6, 3901-3907 (1987)) and/or (ii) the method of Castle & Morris involving the use of a fluorescent substrate (Plant Molecular Biology Manual, B5, 1-16 (1994); S. B. Gelvin & R. A. Schilperoort, Kluwer Academic Publishers). Further, the protein amount is determined by the method of Bradford (Anal. Biochem. 72, 248-254 (1976)). GUS activity is converted based on the protein amount into units of nmole 4-MU/min/mg protein. Thus, the gene expression inducible function can be confirmed for each case.

In addition, if a gene other than the above is used as a reporter gene, the gene transcription level is determined by Northern hybridization, RT-PCR, DNA array technology, or the like. Alternatively, the expression level of the protein encoded by the gene is determined by electrophoresis such as SDS-PAGE, Western blotting, or the like. Thus, the gene expression inducible function can be confirmed.

The gene expression regulatory DNA of the present invention is not limited to the nucleotide sequence shown in SEQ ID NO: 1 or SEQ ID NO: 4. As described in (b) above, it may be a nucleotide sequence that has a deletion, a substitution, an addition, or an insertion of one or a plurality of nucleotides in the nucleotide sequence shown in SEQ ID NO: 1 or SEQ ID NO: 4 as long as it has activity of promoting gene expression in a mature-leaf-specific manner.

For instance, even a nucleotide sequence that has a deletion, a substitution, an addition, or an insertion of 1 to 100 nucleotides, preferably 1 to 50 nucleotides, and more preferably 1 to 10 nucleotides in the nucleotide sequence shown in SEQ ID NO: 1 or SEQ ID NO: 4 is included in the gene expression regulatory DNA of the present invention as long as it shows activity of promoting gene expression in a mature-leaf-specific manner.

In addition, the gene expression regulatory DNA of the present invention is not limited to the nucleotide sequence shown in SEQ ID NO: 1 or SEQ ID NO: 4. As described in (c) above, it may be a nucleotide sequence having 80% or more, more preferably 90% or more, further preferably 95% or more, and most preferably 99% or more sequence identity to the nucleotide sequence shown in SEQ ID NO: 1 or SEQ ID NO: 4 as long as it exhibits activity of promoting gene expression in a mature-leaf-specific manner. Nucleotide sequences can be compared by a generally known method. Comparison can be performed using, for example, BLAST (Basic Local Alignment Search Tool of the National Center for Biological Information in the U.S.) based on default setting.

Further, the gene expression regulatory DNA of the present invention is not limited to the nucleotide sequence shown in SEQ ID NO: 1 or SEQ ID NO: 4. As described in (d) above, it may be a nucleotide sequence that hybridizes under stringent conditions to DNA consisting of a sequence complementary to a part or the entirety of the nucleotide sequence shown in SEQ ID NO: 1 or SEQ ID NO: 4 as long as it shows activity of promoting gene expression in a mature-leaf-specific manner.

Here, the term "stringent conditions" refers to conditions under which namely a specific hybrid is formed, but a non-specific hybrid is never formed. For example, such conditions comprise hybridization at 42 degrees C. to 55 degrees C. in a solution containing 2-6×SSC (1×SSC composition: 0.15 M NaCl, 0.015 M sodium citrate, pH 7.0) and 0.1 to 0.5% SDS, followed by washing at 55 degrees C. to 65 degrees C. in a solution containing 0.1 to 0.2×SSC and 0.1 to 0.5% SDS.

Moreover, the gene expression regulatory DNA of the present invention having activity of promoting gene expression in a mature-leaf-specific manner may be a DNA fragment that has a deletion of 100, 200, 300, 400, 500, 600, 700, 800, 900, 1000, 1100, 1200, 1300, 1400, or 1500 or more consecutive nucleotides from the 5'-end and/or 3'-end in the nucleotide sequence shown in SEQ ID NO: 1 or SEQ ID NO: 4 as long as it exhibits activity of promoting gene expression in a mature-leaf-specific manner. Nucleotides can be deleted by a method generally known to persons skilled in the art (e.g., PCR or restriction enzyme treatment). The DNA fragment may be a promoter region of the gene expression regulatory DNA of the present invention. A promoter region of a predetermined gene expression regulatory DNA can be searched for using a promoter analysis tool generally known to persons skilled in the art (e.g., BioInformatics and Molecular Analysis Section (www-bimas.cit.nih.gov/molbio/proscan/); Prestridge, D. S. (1995), Predicting Pol II Promoter Sequences Using Transcription Factor Binding Sites, J. Mol.

Biol. 249: 923-32). An example of such fragment of the nucleotide sequence shown in SEQ ID NO: 1 and SEQ ID NO: 4 is a DNA consisting of the 1412rd to 1662rd nucleotides of the sequence shown in SEQ ID NO: 1 and a DNA consisting of the 1413rd to 1663rd nucleotides of the sequence shown in SEQ ID NO: 4, respectively. It can be confirmed whether or not the obtained fragment has the gene expression inducible function by the above reporter assay or the like.

Once the nucleotide sequence of the gene expression regulatory DNA of the present invention is determined, it becomes possible to obtain the gene expression regulatory DNA of the present invention by chemical synthesis, PCR using genomic DNA as a template, or hybridization using a DNA fragment having the nucleotide sequence as a probe. Additionally, a nucleotide sequence that has a mutation in the nucleotide sequence shown in SEQ ID NO: 1 or SEQ ID NO: 4 can be synthesized by site-specific mutagenesis or the like. Mutation can be introduced into the nucleotide sequence shown in SEQ ID NO: 1 or SEQ ID NO: 4 by a known technique such as the Kunkel method or the Gapped duplex method or a method based thereof. For example, mutation is introduced with a mutagenesis kit using site-directed mutagenesis (e.g., Mutant-K or Mutant-G (both are trade names of TAKARA Bio)) or the like, or a LA PCR in vitro Mutagenesis series kit (trade name, TAKARA Bio).

Next, a recombinant vector containing the above gene expression regulatory DNA having activity of promoting gene expression in a mature-leaf-specific manner is described.

The recombinant vector of the present invention can be constructed by introducing DNA comprising a desired functional gene operably ligated to the above gene expression regulatory DNA into an appropriate vector. The term "operably ligated" used herein refers to conditions under which the above vector contains the gene expression regulatory DNA and the functional gene ligated to each other such that the functional gene is correctly expressed under the regulation of the gene expression regulatory DNA in a host cell transfected with the above vector. Here, "ligated" may be direct ligation or indirect ligation via a spacer having an appropriate length and an appropriate sequence. Preferable examples of a vector used in the present invention include pBI vectors, pBII vectors, pPZP vectors (Hajdukiewicz P, Svab Z, Maliga P.: The small, versatile pPZP family of *Agrobacterium* binary vectors for plant transformation, Plant Mol Biol., 25: 989-94, 1994), pCAMBIA vectors (www.cambia.org/main/r_et_camvec.htm), and pSMA vectors by which a functional gene can be introduced into a plant using *Agrobacterium*. Particularly preferably, pBI and pBII binary vectors or intermediate vectors are used. Examples of such vectors include pBI121, pBI101, pBI101.2, pBI101.3, pBII221, and pIG121. A binary vector is a shuttle vector replicable in *Escherichia coli* and *Agrobacterium*. When a plant is infected with *Agrobacterium* containing a binary vector, DNA corresponding to a region between border sequences, the LB sequence and the RB sequence, present on the vector can be incorporated into nuclear DNA of the plant (EMBO Journal, 10(3), 697-704 (1991)). Meanwhile, a gene can be directly introduced into a plant using a pUC vector. Examples of a pUC vector include pUC18, pUC19, and pUC9. In addition, plant virus vectors such as cauliflower mosaic virus (CaMV), bean golden mosaic virus (BGMV), and tobacco mosaic virus (TMV) can be used.

In order to facilitate ligation and/or insertion into a vector, DNA comprising the gene expression regulatory DNA and/or DNA comprising the functional gene can be adequately modified with the substitution, insertion, or addition of a restriction enzyme recognition sequence. For insertion into a vector, it is possible to use, for example, a method comprising cleaving purified DNA comprising the gene expression regulatory DNA and/or the functional gene with an adequate restriction enzyme and inserting each obtained fragment into the restriction enzyme recognition site or the multicloning site of adequate vector DNA for ligation to the vector.

The term "functional gene" refers to an arbitrary endogenous gene of a target plant or an arbitrary exogenous gene that is expected to cause expression of a gene product in mature leaves. Examples of such gene include, but are not limited to, a photosynthesis-related gene, a translocation-related gene, a gene capable of producing a useful substance (e.g., a drug, dye, or aromatic component), a sugar metabolism-related gene, a gene with disease/insect resistance (e.g., insect damage resistance, mycotic (fungal) and bacterial disease resistance, or viral (disease) resistance), an environmental stress (e.g., low temperature, high temperature, dry, photolesion, or ultraviolet)-resistance-related gene, and a plant growth regulation (promotion/suppression) gene.

If necessary, an enhancer, an intron, a poly-A addition signal, a 5'-UTR sequence, a selection marker gene, and the like can be ligated upstream/downstream of or between the gene expression regulatory DNA and/or functional gene in the vector.

An enhancer is used to, for example, improve efficiency of functional gene expression. An example thereof is an enhancer region containing a sequence located upstream of a CaMV35S promoter.

A terminator may be a sequence that can terminate transcription of a gene caused by the above promoter. Examples thereof include a nopalin synthetase gene terminator, an octopine synthetase gene terminator, and a CaMV 35S RNA gene terminator.

Examples of a selection marker gene include a hygromycin-resistant gene, a kanamycin-resistant gene, a bialaphos-resistant gene, a blasticidin S-resistant gene, and an acetolactate synthase gene. A selection marker gene may be ligated together with a functional gene to an identical plasmid as described above for preparation of a recombinant vector. Alternatively, a recombinant vector obtained by ligating a selection marker gene to a plasmid and a recombinant vector obtained by ligating a functional gene to a plasmid may be separately prepared. When they are separately prepared, a host is cotransfected with both vectors.

A transformant can be produced using the thus prepared recombinant vector.

When a transformed plant is prepared, various methods that have been reported and established can be adequately used. Preferable examples of such methods include an *Agrobacterium* method, a PEG-calcium phosphate method, an electroporation method, a liposome method, a particle gun method, and a microinjection method. For an *Agrobacterium* method, a protoplast or a tissue section is used or a plant itself is used (in an in planta method). When a protoplast is used, a method comprising coculture of *Agrobacterium* having a Ti plasmid with a protoplast or a method comprising fusion of an *Agrobacterium* spheroplast and a protoplast (i.e., a spheroplast method) is used. When a tissue section is used, a method comprising infecting an aseptic culture leaf section (leaf disc) of a target plant with *Agrobacterium*, a method comprising infecting calluses, or the like with *Agrobacterium* can be used. In addition, if an in planta method using a seed or plant (a system for which tissue culture with the addition of a plant hormone is unnecessary) is employed, water-absorbing seeds, a young plant (young seedling), a potted plant, etc. is directly treated with *Agrobacterium*.

It is possible to confirm the occurrence or nonoccurrence of incorporation of the gene into a plant by a PCR method, a Southern hybridization method, a Northern hybridization method, a Western blotting method, or the like. For example, DNA is prepared from a transformed plant. DNA-specific primers are designed, followed by PCR. After PCR, an amplification product is subjected to agarose gel electrophoresis, polyacrylamide gel electrophoresis, capillary electrophoresis, or the like, followed by staining with ethidium bromide, SYBR Green liquid, or the like. Then, a single band derived from an amplification product is detected. Thus, the occurrence of transformation can be confirmed. In addition, an amplification product can be detected by PCR using primers preliminarily labeled with a fluorescence dye or the like. Further, it is also possible to carry out a method comprising allowing an amplification product to bind to a solid phase such as a microplate and confirming an amplification product via, for example, a fluorescence or enzyme reaction.

Examples of a plant used for transformation in the present invention include, but are not particularly limited to, plants belonging to, for example, the families Gramineae, Solanaceae, Brassicaceae, Leguminosae, Rosaceae, Asteraceae, Liliaceae, Apiaceae, Caryophyllaceae, Cucurbitaceae, Convolvulaceae, and Chenopodiaceae. Preferable examples thereof include the plants belonging to the family Gramineae from which the above gene expression regulatory DNA has been isolated, including sugarcane, rice, barley, wheat, maize, zoysia, *Sorghum*, millet, Japanese millet, napier grass, and switchgrass.

Examples of plant materials subjected to transformation in the present invention include plant tissue of root, stalk, leaf, seed, embryo, ovule, ovary, shoot apex (growth point at the tip of a plant bud), anther, pollen, or the like, a section of such plant tissue, undifferentiated callus, and cultured plant cells such as protoplasts obtained by subjecting the above examples to enzyme treatment for cell wall removal. In addition, when an in planta method is employed, water-absorbing seeds and a plant as a whole can be used.

In addition, the transformed plant in the present invention may be a plant as a whole, a plant organ (e.g., a root, stalk, leaf, petal, seed, or fruit), a plant tissue (e.g., tissue of epidermis, phloem, parenchyma, xylem, or vascular bundle), or a plant culture cell.

When plant culture cells are used, a plant organ or plant itself can be regenerated by a known tissue culture method for regeneration of a transformed plant from the obtained transformed cells. Such regeneration operation can be readily carried out by persons skilled in the art as long as a conventionally known method is used as a method for regeneration of a plant from plant cells. A plant can be regenerated from plant cells as described below.

First, when a plant tissue or protoplast is used as a target plant material for transformation, it is cultured in a sterilized callus formation medium supplemented with inorganic element(s), vitamin(s), carbon source(s), sugar(s) used as energy source(s), plant growth regulator(s) (e.g., a plant hormone such as auxin or cytokinin), and the like for formation of a dedifferentiated callus capable of growing adventitiously (hereinafter referred to as "callus induction"). The thus formed callus is transferred to fresh medium containing a plant growth regulator such as auxin for further growth (subculture).

Callus induction is carried out on a solid medium such as agar. Subculture is carried out via, for example, liquid culture. In such case, each culturing can be carried out efficiently and in large scale. Next, the callus grown by subculture described above is cultured under adequate conditions for induction of organ redifferentiation (hereinafter referred to as "redifferentiation induction"). This eventually results in the regeneration of a complete plant. Redifferentiation induction can be performed by determining the types and amounts of a plant growth regulator such as auxin or cytokinin and different components such as a carbon source to be added to a medium and setting light, temperature, and other conditions in an adequate manner. Such redifferentiation induction results in formation of adventitious embryo, root, bud, stalk leaf, or the like, followed by further cultivation for acquisition of a complete plant. Alternatively, for example, it is possible to preserve a redifferentiated product in a state that would allow it to become a complete plant (e.g., an encapsulated artificial seed, dry embryo, or lyophilization cell or tissue).

According to the present invention, the term "transformed plant" refers to not only a "T1 generation plant" obtained as a first generation plant via redifferentiation after transformation but also a "T2 generation plant" obtained as a plant of the subsequent generation from seeds of the T1 generation plant and a progeny plant such as the next generation (T3 generation) plant obtained via self-pollination of a flower of a "T2 generation" plant that has been found to be a transgenic plant via drug selection, Southern analysis, or the like.

The thus produced transformed plant expresses a functional gene introduced in a mature-leaf-specific manner.

The gene expression regulatory DNA of the present invention has activity of promoting gene expression in a mature-leaf-specific manner in plants, and particularly, sugarcane. A desired functional gene is ligated to the gene expression regulatory DNA of the present invention and the ligation product is introduced into a plant, thereby allowing the functional gene to be expressed in a mature-leaf-specific manner in the plant. Thus, desired properties are imparted to the plant. The gene expression regulatory DNA of the present invention can be appropriately used for sugarcane for which not many gene expression regulatory systems have been developed. The use of the gene expression regulatory DNA of the present invention enables production of transgenic sugarcane having properties appropriate for biomass resources and other applications.

EXAMPLES

The present invention is hereafter described in greater detail with reference to the following examples, although the technical scope of the present invention is not limited thereto.

Example 1

Cloning of Mature Leaf Expression Gene

Total RNA was extracted and purified from mature leaf, young leaf, and stalk tissues of sugarcane (*Saccharum* spp. cv. NiF8) using RNeasy Plant Mini Kits (QIAGEN). A cDNA library was constructed according to a standard method and used for gene expression analysis. Gene expression analysis was carried out using a Sugarcane Genome Array (Affimetrix) according to the manufacturer's instructions.

As a result of gene expression analysis, a gene expressed in mature leaves, young leaves, stalk pith, stalk epidermis, roots, and meristem of *Saccharum* spp. cv. NiF8 was found. The gene was designated as "ecc0001." The nucleotide sequence of the *Saccharum* spp. cv. NiF8-derived ecc0001 gene is identical to the nucleotide sequence of *Saccharum officinarum*-derived ecc0001 EST shown in FIG. 1. Total RNA was extracted and purified from mature leaves, young leaves, stalk pith, stalk leaves, roots, and meristem of *Saccharum* spp. cv. NiF8. cDNA was prepared according to a standard method. The ecc0001 gene expression level in each tissue was analyzed by a SYBRGreen method using an ABI7500 real-time PCR system (Applied Biosystems).

FIG. 2 shows the results. The results shown in FIG. 2 are expressed in relative values with reference to the strongest gene expression level in stalk epidermis, which is designated as 100(%). The expression levels in mature leaves, young leaves, stalk pith, stalk epidermis, roots, and meristem were found to be 12, 13, 90, 100, 17, and 16, respectively. The results revealed that the ecc0001 gene is expressed in mature leaves, young leaves, stalk pith, stalk epidermis, roots, and meristem of *Saccharum* spp. cv. NiF8.

Example 2

Acquisition of Mature-Leaf-Specific Promoter

Genomic DNA (approximately 300 ng) was extracted and purified from mature leaf tissue (0.5 g) of sugarcane (*Saccharum* spp. cv. NiF8) using DNeasy Plant Mini Kits (QIAGEN). The gene expression regulatory region located 5'-upstream of the ecc0001 gene was obtained from the above genomic DNA based on the nucleotide sequence of the ecc0001 gene obtained in Example 1 using RightWalk (registered trademark) Kits (BEX). An HindIII restriction enzyme recognition sequence (AAGCTT) and a BlnI restriction enzyme recognition sequence (CCTAGG) were used as linker sequences. The former was introduced at the 5'-end of the obtained gene expression regulatory region and the latter was introduced on the 3' side of the translation initiation site (ATG) of the ecc0001 gene presented at the 3'-end of the gene expression regulatory region. Thus, DNA comprising the expression regulatory region of the ecc0001 gene was prepared (FIG. 3) (SEQ ID NO: 3).

The above DNA comprising the expression regulatory region of the ecc0001 gene was analyzed using a generally known promoter analysis tool (BioInformatics and Molecular Analysis Section) (www-bimas.cit.nih.gov/molbio/proscan/). As a result, a region capable of functioning as a promoter was presumed to exist in the region comprising the 1419th to 1669th nucleotides (FIGS. 4-1 and 4-2; SEQ ID NO: 5). The region corresponds to the region comprising the 1418th to 1668th nucleotides in the nucleotide sequence shown in SEQ ID NO: 3.

Example 3

Figure 5:
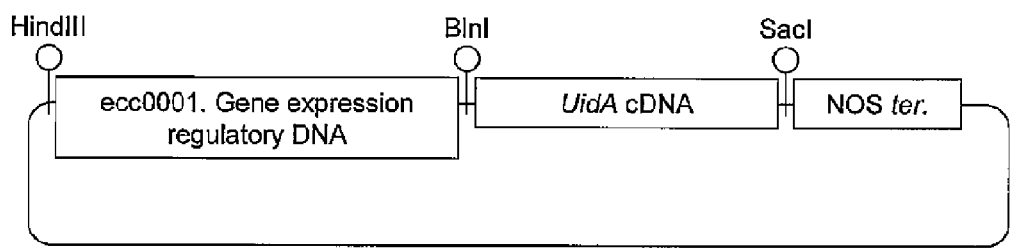
FIG. 5 schematically shows a gene expression vector containing the gene expression regulatory region of the ecc0001 gene and the beta-glucuronidase gene ligated to each other.

Construction of Gene Expression Vector (1) Beta-Glucuronidase Gene Expression Vector A gene expression vector comprising the DNA comprising the gene expression regulatory region obtained in Example 2 (SEQ ID NO:5) ligated to UidAcDNA comprising the beta-glucuronidase (GUS) gene was constructed. A plant transformation vector (pBII221) was used for the gene expression vector. For ligation of the DNA comprising a gene expression regulatory region and UidAcDNA, the ATG sequence encoding the first methionine on the 5'-end side of UidAcDNA and the ATG sequence encoding the first methionine of the ecc0001 gene present on the 3'-end side of the DNA comprising a gene expression regulatory region were matched for ligation (translational fusion type). FIG. 5 schematically shows the gene expression vector.

Example 4

Production of Transgenic Plant

The gene expression vector produced in Example 3 was introduced into a host plant (*Saccharum* spp. cv. NiF8) using an *Agrobacterium* method. Thus, a transgenic sugarcane in which the GUS gene expression was regulated by the expression regulatory DNA of the ecc0001 gene was produced.

Total RNA was extracted and purified from mature leaves, young leaves, stalk pith, stalk epidermis, roots, and meristem of the transgenic sugarcane. cDNA was prepared according to a standard method. The GUS gene expression level in each tissue was analyzed by a SYBRGreen method using an ABI7500 real-time PCR system (Applied Biosystems).

As comparisons, the GUS expression levels in mature leaves and young leaves of the transgenic sugarcane in which the GUS gene expression was regulated by a cauliflower mosaic virus (CaMV)35S promoter and the GUS expression level in meristem of non-transgenic sugarcane (control) were analyzed in the above manner.

Figure 6:
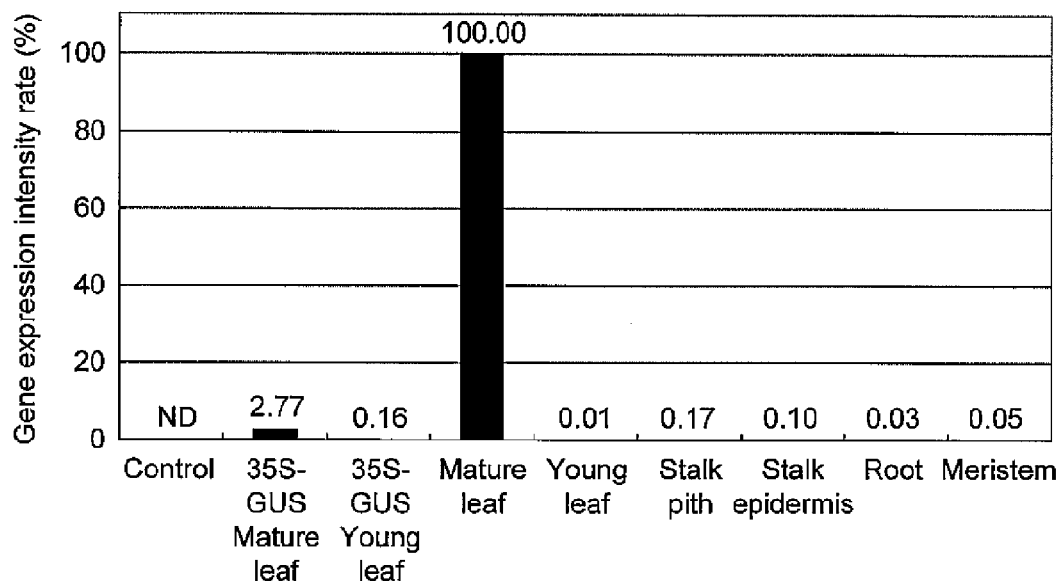
FIG. 6 shows results of beta-glucuronidase gene expression level analysis for individual tissues of a transgenic sugarcane in which the beta-glucuronidase gene expression was regulated by expression regulatory DNA of the ecc0001 gene. The strongest expression level confirmed for mature leaves of the transgenic sugarcane is designated as 100.

FIG. 6 shows the results. The expression levels of the individual tissues are expressed in relative values with reference to the strongest GUS gene expression level confirmed in mature leaves among the analyzed tissues of transgenic sugarcane (in which the GUS gene expression was regulated by the ecc0001 gene expression regulatory DNA), which was designated as 100%.

The above results revealed that the ecc0001 gene expression regulatory DNA can induce gene expression in a mature-leaf-specific manner to an extent approximately 36-fold greater than the GUS gene expression level regulated by a CaMV35S promoter.

INDUSTRIAL APPLICABILITY

The gene expression regulatory DNA of the present invention has activity of promoting gene expression in a mature-leaf-specific manner. Since the DNA has such characteristics, it can be used to produce a plant having desired properties by causing a desired gene to be expressed in a mature-leaf-specific manner.

All publications, patents, and patent applications cited herein are incorporated herein by reference in their entirety.

The invention claimed is:

1. A gene expression regulatory DNA operably linked to a heterologous sequence of interest, wherein the gene expression regulatory DNA comprises a nucleotide sequence shown in SEQ ID NO: 1 or SEQ ID NO: 4; and promotes expression of said heterologous sequence in a mature-leaf-specific manner.

2. A recombinant vector, which comprises the gene expression regulatory DNA according to claim 1.

3. A transformed plant obtained by transformation using the recombinant vector according to claim 2.

4. A transformed plant obtained from plant cells transformed by plant cell transformation using the recombinant vector according to claim 2.

* * * * *

SEQUENCE LISTING

<160> NUMBER OF SEQ ID NOS: 5

<210> SEQ ID NO 1
<211> LENGTH: 2019
<212> TYPE: DNA
<213> ORGANISM: Saccharum spp. cv. NiF8

<400> SEQUENCE: 1

```
gatctgtggt attttggact tctattacaa gtttacagac acagggctca tctgcagtcg    60
gtgggggaga taaggagcga atggaggggc acaaatgtga cgccacgccg gggaaggttc   120
tctgatcgga gtgtattacg gacgggccgt ctgctccgtc ggcgttttgg gcttttgggg   180
tagggcggat ggactcgacg tcggaactac caacatgatg attgatgaac gcgcgcccga   240
cgcattggcg cgtgcgtccg tgcctccgtg cttgctacgc cccaccaacc ttctccacta   300
cgcccggaca aatgccgtgg caaggaggga caacacccac gctaactaac gctcatataa   360
tcaactttgt actatttgta tagttattaa actggcagca ttccaagaaa tgaccgcacg   420
ttaattcctt ctgactgcct attgccaacc gttccttttc tagacccccat ccatccagtt   480
ccaaacaaga tgtattagaa atgcttacat gtgtaaatat atgtacataa atactgcttg   540
cctcgttttt cattcattat ttaaaactat gactgagttt gatatgtagt agttttgcat   600
tgattggcac acaatatgta taatgagagt gtgtcaaact ttcctcctca ttttcactca   660
tccaaattcg atgcacgaat ccctacgccc acaaccgact attaagaata gtccaatttg   720
gcactactct aaatagttgc tggagtttga tgttgtctct ccaactccaa cacggatatc   780
ttgtgcgctc cagctgcaaa accatttatc actacacatt agcatcctcc tcatcctttt   840
cttccaacca tcgcctctca tggtttgcga taaggatggg gtggagcgat ccatgtatct   900
cctctagttc aacttaatga aatatatgtg cgaaaacaag gcaaggaatt gtctaattag   960
ctctttcagt tgaaaccaga ggcgaaccac atatactcat cggaacatca tccccatcct  1020
tagtttggga gacattgatc tcatgatctg tcaaggcgtt agagctagcg ttgccttgtt  1080
gaacattggc tttgatgttg caaagactac atcgcttcat taagggtcg aagacgtgga  1140
aattgtgcag gacgaagcaa aagccacaca ctgcgttgtt tgaatacttc accgtaattc  1200
ttggttcaag ctttgagcat acaaccagaa tcaatcttgt cttgaagcct tagtcttgca  1260
atccaccaac ctcagcgacc ttgacgcttg cttctcggag gcaaaagttt tgtcagtgat  1320
caatgacatt tcatcagaca aggcgacatt accggacggg ttcactgggc tcttctacca  1380
acgccgcatc aaacaagccc cagagatgta aaacaaacag tttatataca taattaaaac  1440
tagtaaattc aagcgtggcc gagtgaatct caagctgacg tgtgtagttc ccgccgtcgc  1500
actcaagaaa ggtcaaaggt ggacacgaat ctcaaagcaa tgcatatgca tatgcacatg  1560
cacaagcaca cccgacgtc cccgtgccag acccggtggc ccaccggatg aagtacgtac  1620
cgaattagca gatggaggaa tcttcttcgg ttgagacgtt gctttccgct acaccttctc  1680
tgccagtctg ctgtctgctc tgctgcaggc tgtctgctag ctgagccctg caggtgatgt  1740
gctagctttt gagtggcaca tgcgctgtgt ttgtgtagtc tagtgtagcc ggcgtagcaa  1800
cgcttggtgt gccactaccg attttaaaag ccattacgct ttcctacacc gcacggctca  1860
gtcacccacc cacccactca ctcagaacga aagcccccagc aagctcagct cagctgctca  1920
cacctcacac ccacaggcca cactcacagc ggagcagagt agtgagcact gagcagggca  1980
gcagagcgcg cggtcagttc aggtcgatcg tcagccatg                         2019

<210> SEQ ID NO 2
<211> LENGTH: 1321
<212> TYPE: DNA
<213> ORGANISM: Saccharum officinarum

<400> SEQUENCE: 2
acgcacccag ccactcactc agaacgaaag ccccagcaag ctcagctcag ctgctcacac    60
```

| | |
|---|---|
| ctcacaccca caggccacac tcacagcgga gcagagtagt gagcactgag cagggcagca | 120 |
| gagcgcgcgg tcagttcagg tcgatcgtca gccatgagca aggatgacaa gcaccaccgc | 180 |
| cacgagcacc acctgcgtcg ctgctgcggg tgcatggcgt cgtgcctgct ggcgctggtc | 240 |
| ctcatcgtcg ccttcatcgc gctggtcatc tacctcgccc tccgcccctc gaagccgtcc | 300 |
| ttctacctgc aggacctgca gctgcggcgg cccatctcgc tggccgaccc gtcgctgacg | 360 |
| gcgtcggcgc aggtgacgct ggcgtcccgc aacccaacg agcacgtggg catcttctac | 420 |
| aagcgcctgg acgtgttcgt gacctaccag aacgaggcgg tcacggtgcc cgtgtcgctg | 480 |
| ccgccgcagt accagggcca ccgcgacgtc accgtctggt cccccgtgct gtcggccgag | 540 |
| tccgtgcccg tggccggcta cgtcgccgac gacctcaagc gtgacgtcgc ggccggcttc | 600 |
| gtcgctctgc aggtcaaggt ggacggccgc gtcaagtgga aggtcggcag ctgggtctcc | 660 |
| gggagctacc acctcttcgt cagctgcccc gccgtgctct ccgcggggta ccccggcgtc | 720 |
| gtgggcggcg cggcaacaa caccgtgtcg tcgctcaagt tcgcgcagcc cacgggatgc | 780 |
| agcgtcgagg tgtgatgtga tccactgatg acgcactcaa gaacagttgc caagtactgc | 840 |
| tactcaaatt tctttgggta caccgttaat tacgctgtta attttgttca tgtctcattc | 900 |
| tcaattctca ttctcttgtg gggaataagt ttctgtcgca ggccatatag ctgttcaaaa | 960 |
| acttgaagtc aattgtacca acatgtgttt attcaaagaa gaaagaggg ccactgcaaa | 1020 |
| aacatacata gatgcgctaa ccccgagcat gctcaaaact agaagaactc ccaccgacgc | 1080 |
| ctatagtggc gactgaatac tgccacaaac tcgggggggg cgcctaaaag attcacatct | 1140 |
| aatttcgctg tgtggaaaga attaatcctc tcggaggggc ccaaaaataa ggcaccgggc | 1200 |
| cccagtttaa aagaggatga ggggagaaac accggcgttc acaaaatata atgcccttga | 1260 |
| cagtaaaccc tccttctac catggggtgt ataaacaata aaggccaca cctataaggc | 1320 |
| c | 1321 |

<210> SEQ ID NO 3
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 3

| | |
|---|---|
| aagcttgatc tgtggtattt tggacttcta ttacaagttt acagacacag ggctcatctg | 60 |
| cagtcggtgg gggagataag gagcgaatgg aggggcacaa atgtgacgcc acgccgggga | 120 |
| aggttctctg atcggagtgt attacggacg ggccgtctgc tccgtcggcg ttttgggctt | 180 |
| ttggggtagg gcggatggac tcgacgtcgg aactaccaac atgatgattg atgaacgcgc | 240 |
| gcccgacgca ttggcgcgtg cgtccgtgcc tccgtgcttg ctacgcccca ccaaccttct | 300 |
| ccactacgcc cggacaaatg ccgtggcaag gagggacaac acccacgcta actaacgctc | 360 |
| atataatcaa cttgtgtacta tttgtatagt tattaaactg gcagcattcc aagaaatgac | 420 |
| cgcacgttaa ttccttctga ctgcctattg ccaaccgttc cttttctaga ccccatccat | 480 |
| ccagttccaa acaagatgta ttagaaatgc ttacatgtgt aaatatatgt acataaatac | 540 |
| tgcttgcctc gttttcatt cattatttaa aactatgact gagtttgata tgtagtagtt | 600 |
| ttgcattgat tggcacacaa tatgtataat gagagtgtgt caaactttcc tcctcatttt | 660 |
| cactcatcca aattcgatgc acgaatccct acgccacaa ccgactatta agaatagtcc | 720 |
| aatttggcac tactctaaat agttgctgga gtttgatgtt gtctctccaa ctccaacacg | 780 |

```
gatatcttgt gcgctccagc tgcaaaacca tttatcacta cacattagca tcctcctcat    840
cctttcttc caaccatcgc ctctcatggt ttgcgataag gatggggtgg agcgatccat     900
gtatctcctc tagttcaact taatgaaata tatgtgcgaa acaaggcaa ggaattgtct     960
aattagctct ttcagttgaa accagaggcg aaccacatat actcatcgga acatcatccc  1020
catccttagt ttgggagaca ttgatctcat gatctgtcaa ggcgttagag ctagcgttgc  1080
cttgttgaac attggctttg atgttgcaaa gactacatcg cttcattaag gggtcgaaga  1140
cgtggaaatt gtgcaggacg aagcaaaagc cacacactgc gttgtttgaa tacttcaccg  1200
taattcttgg ttcaagcttt gagcatacaa ccagaatcaa tcttgtcttg aagccttagt  1260
cttgcaatcc accaacctca gcgaccttga cgcttgcttc tcggaggcaa agttttgtc   1320
agtgatcaat gacatttcat cagacaaggc gacattaccg gacgggttca ctgggctctt  1380
ctaccaacgc cgcatcaaac aagccccaga gatgtaaaac aaacagttta tatacataat  1440
taaaactagt aaattcaagc gtggccgagt gaatctcaag ctgacgtgtg tagttcccgc  1500
cgtcgcactc aagaaaggtc aaaggtggac acgaatctca aagcaatgca tatgcatatg  1560
cacatgcaca agcacaaccc gacgtccccg tgccagaccc ggtggcccac cggatgaagt  1620
acgtaccgaa ttagcagatg gaggaatctt cttcggttga acgttgcttt ccgctacac   1680
cttctctgcc agtctgctgt ctgctctgct gcaggctgtc tgctagctga gccctgcagg  1740
tgatgtgcta gcttttgagt ggcacatgcg ctgtgtttgt gtagtctagt gtagccggcg  1800
tagcaacgct tggtgtgcca ctaccgattt taaaagccat tacgctttcc tacaccgcac  1860
ggctcagtca cccacccacc cactcactca gaacgaaagc cccagcaagc tcagctcagc  1920
tgctcacacc tcacacccac aggccacact cacagcggag cagagtagtg agcactgagc  1980
agggcagcag agcgcgcggt cagttcaggt cgatcgtcag ccatgcctag g            2031
```

<210> SEQ ID NO 4
<211> LENGTH: 2044
<212> TYPE: DNA
<213> ORGANISM: Saccharum spp. cv. NiF8

<400> SEQUENCE: 4

```
gatctgtggt attttggact tctattacaa gtttacagac acagggctca tctgcagtcg    60
gtggggaga taaggagcga atggaggggc acaaatgtga cgccacgccg gggaaggttc    120
tctgatcgga gtgtattacg gacgggccgt ctgctccgtc ggcgttttgg gcttttgggg   180
tagggcggat ggactcgacg tcggaactac caacatgatg attgatgaac gcgcgcccga   240
cgcattggcg cgtgcgtccg tgcctccgtg cttgctacgc cccaccaacc ttctccacta   300
cgcccggaca aatgccgtgg caaggaggga caacacccac gctaactaac gctcatataa   360
tcaactttgt actatttgta tagttattaa actggcagca ttccaagaaa tgaccgcacg   420
ttaattcctt ctgactgcct attgccaacc gttcctttc tagaccccat ccatgccagt    480
tccaaacaag atgtattaga aatgcttaca tgtgtaaata tatgtacata atactgctt    540
gcctcgtttt tcattcatta tttaaaacta tgactgagtt tgatatgtag tagttttgca   600
ttgattggca cacaatatgt ataatgagag tgtgtcaaac tttcctcctc attttcactc   660
atccaaattc gatgcacgaa tccctacggc acaaccgac tattaagaat agtccaattt    720
ggcactactc taaatagttg ctggagtttg atgttgtctc tccaactcca acacggatat   780
cttgtgcgct ccagctgcaa aaccatttat cactacacat tagcatcctc ctcatccttt   840
```

```
tcttccaacc atcgcctctc atggtttgcg ataaggatgg ggtggagcga tccatgtatc    900
tcctctagtt caacttaatg aaatatatgt gcgaaaacaa ggcaaggaat tgtctaatta    960
gctctttcag ttgaaaccag aggcgaacca catatactca tcggaacatc atccccatcc   1020
ttagtttggg agacattgat ctcatgatct gtcaaggcgt tagagctagc gttgccttgt   1080
tgaacattgg ctttgatgtt gcaaagacta catcgcttca ttaagggtc gaagacgtgg    1140
aaattgtgca ggacgaagca aaagccacac actgcgttgt ttgaatactt caccgtaatt   1200
cttggttcaa gctttgagca tacaaccaga atcaatcttg tcttgaagcc ttagtcttgc   1260
aatccaccaa cctcagcgac cttgacgctt gcttctcgga ggcaaaagtt ttgtcagtga   1320
tcaatgacat ttcatcagac aaggcgacat taccggacgg gttcactggg ctcttctacc   1380
aacgccgcat caaacaagcc ccagagatgt aaaacaaaca gtttatatac ataattaaaa   1440
ctagtaaatt caagcgtggc cgagtgaatc tcaagctgac gtgtgtagtt cccgccgtcg   1500
cactcaagaa aggtcaaagg tggacacgaa tctcaaagca atgcatatgc atatgcacat   1560
gcacaagcac aacccgacgt ccccgtgcca gacccggtgg cccaccggat gaagtacgta   1620
ccgaattagc agatggagga atcttcttcg gttgagacgt tgctttccgc tacaccttct   1680
ctgccagtct gctgtctgct ctgctgcagg ctgtctgcta gctgagccct gcagcgaggg   1740
ttaaccaatc gtccattcgt gatgtgctag cttttgagtg gcacatgcgc tgtgtttgtg   1800
tagtctagtg tagccggcgt agcaacgctt ggtgtgccac taccgatttt aaaagccatt   1860
acgctttcct acaccgcacg gctcagtcac ccacccaccc actcactcag aacgaaagcc   1920
ccagcaagct cagctcagct gctcacacct cacacccaca ggccacactc acagcggagc   1980
agagtagtga gcactgagca gggcagcaga gcgcgcggtc agttcaggtc gatcgtcagc   2040
catg                                                                 2044
```

<210> SEQ ID NO 5
<211> LENGTH: 2056
<212> TYPE: DNA
<213> ORGANISM: Artificial Sequence
<220> FEATURE:
<223> OTHER INFORMATION: Synthetic polynucleotide

<400> SEQUENCE: 5

```
aagcttgatc tgtggtattt tggacttcta ttacaagttt acagacacag ggctcatctg     60
cagtcggtgg gggagataag gagcgaatgg aggggcacaa atgtgacgcc acgccgggga   120
aggttctctg atcggagtgt attacggacg ggccgtctgc tccgtcggcg ttttgggctt    180
ttggggtagg gcggatggac tcgacgtcgg aactaccaac atgatgattg atgaacgcgc    240
gcccgacgca ttggcgcgtg cgtccgtgcc tccgtgcttg ctacgcccca ccaaccttct    300
ccactacgcc cggacaaatg ccgtggcaag gagggacaac acccacgcta actaacgctc    360
atataatcaa ctttgtacta tttgtatagt tattaaactg gcagcattcc aagaaatgac    420
cgcacgttaa ttccttctga ctgcctattg ccaaccgttc cttttctaga ccccatccat    480
gccagttcca acaagatgt attagaaatg cttacatgtg taaatatatg tacataaata    540
ctgcttgcct cgttttttcat tcattattta aaactatgac tgagtttgat atgtagtagt    600
tttgcattga ttggcacaca atatgtataa tgagagtgtg tcaaactttc ctcctcattt    660
tcactcatcc aaattcgatg cacgaatccc tacggccaca accgactatt aagaatagtc    720
caatttggca ctactctaaa tagttgctgg agtttgatgt tgtctctcca actccaacac    780
ggatatcttg tgcgctccag ctgcaaaacc atttatcact acacattagc atcctcctca    840
```

-continued

```
tccttttctt ccaaccatcg cctctcatgg tttgcgataa ggatggggtg gagcgatcca    900
tgtatctcct ctagttcaac ttaatgaaat atatgtgcga aaacaaggca aggaattgtc    960
taattagctc tttcagttga aaccagaggc gaaccacata tactcatcgg aacatcatcc   1020
ccatccttag tttgggagac attgatctca tgatctgtca aggcgttaga gctagcgttg   1080
ccttgttgaa cattggcttt gatgttgcaa agactacatc gcttcattaa ggggtcgaag   1140
acgtggaaat tgtgcaggac gaagcaaaag ccacacactg cgttgtttga atacttcacc   1200
gtaattcttg gttcaagctt tgagcataca accagaatca atcttgtctt gaagccttag   1260
tcttgcaatc caccaacctc agcgaccttg acgcttgctt ctcggaggca aaagttttgt   1320
cagtgatcaa tgacatttca tcagacaagg cgacattacc ggacgggttc actgggctct   1380
tctaccaacg ccgcatcaaa caagcccag agatgtaaaa caaacagttt atatacataa   1440
ttaaaactag taaattcaag cgtggccgag tgaatctcaa gctgacgtgt gtagttcccg   1500
ccgtcgcact caagaaaggt caaggtgga cacgaatctc aaagcaatgc atatgcatat   1560
gcacatgcac aagcacaacc cgacgtcccc gtgccagacc cggtggccca ccggatgaag   1620
tacgtaccga attagcagat ggaggaatct tcttcggttg agacgttgct ttccgctaca   1680
ccttctctgc cagtctgctg tctgctctgc tgcaggctgt ctgctagctg agccctgcag   1740
cgagggttaa ccaatcgtcc attcgtgatg tgctagcttt tgagtggcac atgcgctgtg   1800
tttgtgtagt ctagtgtagc cggcgtagca acgcttggtg tgccactacc gattttaaaa   1860
gccattacgc tttcctacac cgcacggctc agtcacccac ccaccactc actcagaacg   1920 aaagccccag caagctcagc tcagctgctc acacctcaca cccacaggcc acactcacag   1980
cggagcagag tagtgagcac tgagcagggc agcagagcgc gcggtcagtt caggtcgatc   2040
gtcagccatg cctagg                                                   2056
```